(12) United States Patent
Sanseverino et al.

(10) Patent No.: US 10,993,610 B2
(45) Date of Patent: May 4, 2021

(54) MAGNETIC LIGHT GUIDE PLUG CONNECTION

(71) Applicant: Oertli-Instrumente AG, Berneck (CH)

(72) Inventors: Flavio Sanseverino, Au (SG) (CH); Norbert Brill, Kreuzlingen (CH)

(73) Assignee: Oertli-Instrumente AG, Berneck (CH)

( * ) Notice: Subject to any disclaimer, the term of this patent is extended or adjusted under 35 U.S.C. 154(b) by 256 days.

(21) Appl. No.: 15/596,343

(22) Filed: May 16, 2017

(65) Prior Publication Data

US 2017/0332895 A1 Nov. 23, 2017

(30) Foreign Application Priority Data

May 18, 2016 (EP) ..................................... 16170109

(51) Int. Cl.
*A61B 3/00* (2006.01)
*A61B 90/30* (2016.01)
(Continued)

(52) U.S. Cl.
CPC .......... *A61B 3/0008* (2013.01); *A61B 3/0016* (2013.01); *A61B 90/30* (2016.02);
(Continued)

(58) Field of Classification Search
CPC ....... A61B 3/00; A61B 3/0008; A61B 3/0016; A61B 2090/306; A61B 2090/309; A61B 2017/00477; A61B 2017/00831; A61B 2017/00876; A61B 2017/347; A61B 2018/00196; A61B 17/3462; A61B 18/22; A61B 1/00112; A61B 1/00117; A61B 1/00121; A61B 1/00124; A61B 1/00126; A61B 90/30; A61F 9/007; A61F 9/008;
(Continued)

(56) References Cited

U.S. PATENT DOCUMENTS

| 4,250,128 A | * | 2/1981 | Meckling | ................ | C04B 35/26 |
|---|---|---|---|---|---|
| | | | | | 264/108 |
| 2006/0063974 A1 | * | 3/2006 | Uchiyama | .......... | A61B 1/00057 |
| | | | | | 600/114 |

(Continued)

FOREIGN PATENT DOCUMENTS

| EP | 2975440 A1 | 1/2016 |
|---|---|---|
| JP | 200592082 A | 4/2005 |

(Continued)

*Primary Examiner* — James C. Jones
(74) *Attorney, Agent, or Firm* — The Webb Law Firm

(57) ABSTRACT

An ophthalmic light instrument includes a plug (1) and a light guide (7) for guiding light (10) to a surgical site in the eye. The plug (1) is configured to be magnetically attractable or attractive and can be positioned and connected releasably with respect to a light source in such a way, that coupling of the light (10) into the light instrument takes place at the focal point (14) of the light source (12). An ophthalmic illumination system includes such a light instrument and a socket of the light source. The socket of the light source (4) is configured to be magnetically attractable or attractive and can be positioned and connected releasably with respect to the light source in such a way, that coupling of the light (10) into the light instrument takes place at the focal point (14) of the light source (12).

21 Claims, 6 Drawing Sheets

(51) Int. Cl.
  *G02B 6/36* (2006.01)
  *G02B 6/42* (2006.01)
  *A61B 1/00* (2006.01)
  *A61B 17/00* (2006.01)
  *A61F 9/007* (2006.01)

(52) U.S. Cl.
  CPC ......... *G02B 6/3624* (2013.01); *G02B 6/4204* (2013.01); *G02B 6/4292* (2013.01); *A61B 1/00126* (2013.01); *A61B 2017/00876* (2013.01); *A61B 2090/306* (2016.02); *A61F 9/007* (2013.01)

(58) Field of Classification Search
  CPC .. A61F 9/00; G02B 6/26; G02B 6/262; G02B 6/36; G02B 6/3616; G02B 6/38; G02B 6/3873; G02B 6/3801; G02B 6/3809; G02B 6/3886; G02B 6/42; G02B 23/2469; G02B 6/3624; G02B 6/4204; G02B 6/4292
  USPC ................... 351/221; 606/4, 13, 15, 16, 27
  See application file for complete search history.

(56) References Cited

U.S. PATENT DOCUMENTS

| | | |
|---|---|---|
| 2007/0191823 A1 | 8/2007 | Scheller |
| 2009/0116791 A1* | 5/2009 | Thyzel ................ G02B 6/4292 385/66 |
| 2009/0275930 A1* | 11/2009 | Di Sessa ................ A61B 18/22 606/13 |
| 2016/0087726 A1 | 3/2016 | Roberds et al. |

FOREIGN PATENT DOCUMENTS

| | | |
|---|---|---|
| WO | 2005048817 A2 | 6/2005 |
| WO | 2012154435 A1 | 11/2012 |

* cited by examiner

MAGNETIC LIGHT GUIDE PLUG CONNECTION

CROSS-REFERENCE TO RELATED APPLICATION

This application claims priority to European Patent Application No. 16,170,109.9 filed May 18, 2016, the disclosure of which is hereby incorporated in its entirety by reference.

BACKGROUND OF THE INVENTION

Field of the Invention

The present invention relates to an ophthalmic light instrument, and to an ophthalmic illumination system comprising such a light instrument.

Description of Related Art

In eye surgery, sufficient illumination of the interior of the eye or of the background of the eye is of great importance. However, the human eye reacts very sensitively to blue, violet or UV light and is damaged by an excessively high light intensity. If the light intensity is too high, or a particular light dose is exceeded, the eye may be thermally or photochemically damaged within a short time. For endoillumination in eye surgery, fibre-optic light guides are often used, which are inserted into the eye through a small incision in the "pars plana".

WO 2012/154435 A1 discloses an illuminated microsurgical instrument, which has a glass optical fibre with a bevelled end face. The refractive index of the optical fibre is in this case greater than the refractive index of the eye, such that angular distribution of the emitted light beam takes place in the eye.

WO 2005/048817 A2 discloses an illuminated laser probe with an adjustable illumination region, a mechanism being actively connected to the laser probe in order to move the laser fibre between a retracted position and an extended position.

However, light guides or light probes often illuminate the intraocular space insufficiently, so that a plurality of light probes are used, further light guides are employed, or the light probes need to be repositioned during the operation. This may be disadvantageous for the patient, because the operation therefore lasts longer or possibly cannot be carried out so accurately. Furthermore, the coupling of the light probes or light guides to a light source may require a complicated or elaborate coupling mechanism, for which the surgical staff need to carry out fixing, for example manually, by means of an interlocking connection. Less elaborate coupling may for example be produced by clamping the light probe or light guide to the light source, although this involves abutment instead of firm fixing. In this case, however, the risk arises that the coupling is insufficient and the light probe or the light guide will move or even become detached from the light source.

SUMMARY OF THE INVENTION

It is therefore the object of the invention to provide an ophthalmic light instrument and/or an ophthalmic illumination system, which overcomes the disadvantages of the prior art. In particular, the ophthalmic light instrument or system is intended to allow improved coupling to a light source.

In a first aspect, an ophthalmic light instrument is provided, which comprises a plug of the light instrument, having an abutment surface, and a light guide, mounted on the plug of the light instrument, for guiding light, or a light beam, to a surgical site in the eye, wherein the light guide has a proximal end for coupling of light from a light source and a distal end for emission of light. The plug of the light instrument is configured to be magnetically attractable or attractive and can be positioned by means of its abutment surface with respect to the light source in such a way, and can be connected releasably to the light source in such a way, that the proximal end of the light guide comes to lie at the focal point of the light source, so that a coupling of the light into the light instrument takes place at the focal point of the light source.

During the continual manipulations by an operator, the plug of the light instrument may be pulled out of the focal point by the tensile stress transmitted through the light guide, which leads to reduced or in the worst case even interrupted illumination at the surgical intervention site in the eye. By virtue of the fact that the plug of the light instrument is configured to be magnetically attractable or attractive, and magnetic attraction therefore takes place, the magnetic attraction corrects or prevents this behaviour. The light instrument can therefore be coupled simply and reliably to a light source because of the magnetic attraction.

When a tensile stress acts on the plug of the light instrument, the plug may be moved away from the light source. By virtue of the magnetically attractable or attractive design, after the action of the tensile stress on the light instrument, the plug of the light instrument is therefore positioned, or held, again by its abutment surface with respect to the light source in such a way that the coupling of light into the light instrument takes place at the focal point of the light source. The coupling side of the light instrument therefore always lies at the focal point of the light source, which ensures a maximal light power/illumination as well as stable and reproducible light power of the light instrument. The light instrument therefore ensures improved and reliable illumination conditions at the surgical intervention site in the eye.

Furthermore, the magnetically attractive or attractable plug of the light instrument allows simple positioning and releasable connection to the light source, since no interlocking mechanisms such as screw or bayonet connections need to be actuated for this purpose, and because of the magnetic force only a small exertion of force by the operator is needed for the coupling to the light source. The light instrument therefore has easy handling.

In one preferred variant, the light instrument may be an illumination element which is provided exclusively for illumination. As an alternative, however, the light instrument may also be an integral part of an illuminated instrument, for example an illuminated cutter, an illuminated laser probe, illuminated forceps, etc.

The expression that the light guide is mounted on the plug of the light instrument includes all types of mounting of the light guide on the plug of the light instrument. For example, the light guide may be mounted inside the plug of the light instrument or on an outer face of the plug of the light instrument.

Preferably, the light guide is mounted firmly, i.e. in such a way that it cannot move with respect to the plug of the light instrument. The light guide may, for example, be mounted with a material fit on the plug of the light instrument by means of an adhesive.

As an alternative, the light guide may be mounted firmly in a guide tube, which extends through the plug and is firmly connected to the plug. This means that the light guide is connected to the plug by means of the guide tube. The guide tube encloses the light guide in the manner of a sleeve. The guide tube may, for example, be made of metal or plastic. Preferably, the guide tube extends with its proximal end out of the plug of the light instrument, so that the guide tube can be inserted into a socket. The distal end of the guide tube may also protrude from the interior of the plug.

At the distal end of the light guide, the light guide preferably comprises a handle, which can be gripped by the surgical staff.

Magnetism is a physical phenomenon which is manifested, in particular, as a force action between magnets, magnetised or magnetisable objects and moving electrical charges. This force is mediated by a magnetic field, which on the one hand is generated by these objects and on the other hand acts on them. Diamagnetism, paramagnetism and ferromagnetism refer to various magnetic properties of matter. A ferromagnetic material can be attracted strongly by a magnet. A paramagnetic material, on the other hand, can be attracted only very weakly, and a diamagnetic material may even be weakly repelled.

The magnetic properties of matter are explained by elementary magnets, this predominantly involving electron spins or nuclear spins, which as atomic spins have a magnetic action. The magnetic forces of permanent magnets or constant magnets are explained by the elementary magnets of the individual atoms of the material being aligned parallel. This parallel alignment of the atomic spins occurs in ferromagnetic materials. The alignment of the elementary magnets may, for example, be disrupted by input of heat energy or by application of an oppositely directed external magnetic field. This is referred to as demagnetisation.

In this context, "magnetically attractable" and "magnetically attractive" are intended to mean that the magnetically attractable material component is attracted by the magnetically attractive material component because of the magnetic attraction force.

In one variant, the plug of the light instrument preferably comprises a magnetisable material component or a magnetised material component. In this case, the plug of the light instrument may interact with a magnetically attractable material component on the light source. In another variant, the plug of the light instrument comprises a magnetically attractable material component. In this case, the plug of the light instrument may interact with a magnetisable or magnetised material component on the light source.

In this case, it should be understood that a "material component" is intended to mean a component of magnetisable or magnetised or magnetic material in relation to the rest of the material, in which case this component may be relatively small, i.e. essentially no component of magnetisable or magnetised or magnetic material, or large, i.e. a large component of magnetisable or magnetised or magnetic material, or the entire amount, i.e. fully made of magnetisable or magnetised or magnetic material.

The magnetisable material component in the plug of the light instrument may be magnetised.

If a material is exposed to an external magnetic field, magnetisation of the material takes place. The direction and strength of this magnetisation are in this case based on intrinsic properties of the material, so that the magnetisation of matter in an external field, i.e. the alignment of the elementary magnets in the material, is parallel or antiparallel to the external magnetic field. A ferromagnetic material is itself magnetised in an external magnetic field. Nonferromagnetic materials, for example diamagnets and paramagnets, may also be magnetised, although the effect is much weaker in these materials. Furthermore, in diamagnets and paramagnets, the magnetisation disappears again when the external magnetic field is turned off, but not in ferromagnetic materials.

The magnetisable material component and/or the magnetised material component may consist of ferrimagnetic material, and/or the magnetisable material component and/or the magnetised material component may consist of ferromagnetic material.

A material is termed ferromagnetic if, in an external magnetic field, it exhibits an intrinsic, so-called spontaneous magnetisation which is independent of the external magnetic field. The external magnetic field determines the direction of the elementary magnets, whereas their magnitude is independent thereof. Different from this is ferrimagnetism, in which the elementary magnets are respectively directed alternately oppositely and are differently strong in the two directions, for which reason a magnetisation remains for each pair. The macroscopic behaviour of ferrimagnetic materials is therefore a weaker form of ferromagnetism.

In one particularly preferred embodiment, the magnetisable material component and/or the magnetised material component and/or the magnetically attractive material component is preferably particularly configured and is embedded in a plastic matrix. The plug of the light instrument is thus essentially produced from plastic with embedded magnetisable or magnetised particles. The plastic matrix is preferably produced by injection moulding or extrusion, in which case the particles can be embedded during the injection moulding or the extrusion.

The magnetisable material component may be magnetised during the injection moulding or during the extrusion by application of a magnetic field.

Thus, for example, the plug of the light instrument may be produced from ferrite particles which are bound in plastic, the ferrite particles being already magnetised or nonmagnetised, or the ferrite particles being exposed to an external magnetic field during the production process and thereby magnetised for the first time.

Production of the plug of the light instrument as an injection-moulded or extruded part allows economical production in large batch numbers. In particular, the plug of the light instrument is therefore suitable as a disposable part, which is of great importance particularly in respect of the requirements relating to hygiene and sterility of an operating theatre.

The magnetically attractable and particulate material component contains for example iron, nickel and/or cobalt. Besides this the magnetically attractable and particulate material component may consist of alloys (for example samarium-cobalt or neodymium-iron-boron).

The plug of the light instrument may consist fully of the magnetisable material component or of the magnetised material component.

It is, however, also conceivable for the magnetisable material component or the magnetised material component to be arranged in the region of the proximal end of the plug of the light instrument, particularly in the abutment surface of the plug of the light instrument.

In other words, the magnetisable material component or the magnetised material component, for example ferrite particles, may be incorporated into a plastic material only in regions.

It is also conceivable for the magnetised material component to be configured as at least one magnet or as at least one solenoid.

This means that, instead of or in addition to the magnetisable or magnetised particulate material component, a constant magnet, also referred to as a permanent magnet, and/or a solenoid is thus introduced into the plug of the light instrument or attached thereto. For example, such a permanent magnet or solenoid may be attached or introduced in the proximal region of the plug of the light instrument, for example in the abutment surface of the plug of the light instrument.

The plug of the light instrument preferably has an essentially cylindrical body, which internally defines a cavity. The cavity preferably opens into an entry orifice at the proximal end and into an exit orifice at the distal end of the plug of the light instrument, the light guide extending through the entry orifice, via the cavity, and through the exit orifice.

It is preferred that in this case the light guide is firmly mounted in the interior of the plug of the light instrument, particularly in the region of the entry and exit orifices of the plug of the light instrument.

Preferably, the abutment surface at the proximal end of the plug of the light instrument is configured as a flange, the diameter of which is greater than the diameter of the essentially cylindrical body of the plug of the light instrument.

It is, however, also conceivable for the flange and the essentially cylindrical body of the plug of the light instrument to have the same diameter, i.e. the abutment surface together with the body form a plug of the light instrument in a cylindrical configuration with a constant diameter.

It is in this case preferred for the essentially cylindrical body of the plug of the light instrument and the abutment surface configured as a flange to be formed in one piece and, for example, to be produced as a single injection-moulded or extruded part during the production method by injection moulding or extrusion.

Preferably, the cavity has two sections of different diameter. In a first section, the cavity has a diameter which essentially corresponds to the external diameter of the light guide. In this first section, the light guide is mounted in the cavity. In a second section, which follows on from the first section, the cavity has a diameter which is greater than that of the first section. The enlarged configuration has the advantage that bends of the light guide can be avoided.

In other words, as seen in the distal direction, i.e. starting from the light source in the direction of the plug of the light instrument, the second section follows on distally from the first section. The first section of the cavity therefore opens into the entry orifice at the proximal end of the plug of the light instrument, whereas the second section of the cavity opens into the exit orifice at the distal end of the plug of the light instrument.

In a further aspect, an ophthalmic illumination system is provided, comprising a light instrument as described above and a socket of the light source, having a further abutment surface. The socket of the light source is configured to be magnetically attractable or attractive, particularly in a manner corresponding to the plug of the light instrument. The abutment surface of the plug of the light instrument comes in contact with the further abutment surface of the socket of the light source, so that the socket of the light source can be positioned with respect to the light source in such a way, and can be connected releasably to the plug of the light instrument in such a way, that the proximal end of the light guide comes to lie at the focal point of the light source, so that coupling of the light into the light instrument takes place at the focal point of the light source.

By the plug of the light instrument being configured to be magnetically attractable or attractive and the socket of the light source being configured to be magnetically attractive or attractable, the magnetic attraction force between the plug of the light instrument and the socket of the light source ensures that the plug of the light instrument always rests with its abutment surface on the further abutment surface of the socket of the light source, and the illumination system can therefore be coupled simply and reliably in relation to the socket of the light source and the plug of the light instrument, and therefore in relation to a light source.

As mentioned above, during the continual manipulations by an operator, the light instrument may be pulled out of the focal point of the light source by the tensile stress, which leads to reduced or in the worst case even interrupted illumination at the surgical intervention site in the eye. The magnetic attraction force between the plug of the light instrument and the socket of the light source corrects this behaviour, and the coupling side of the light instrument therefore always lies at the focal point of the light source, which ensures a maximal light power/illumination as well as a stable and reproducible light power of the illumination system, while the light guide remains undamaged in spite of high tensile stresses. The illumination system therefore ensures improved and reliable illumination conditions at the surgical intervention site in the eye.

Furthermore, the magnetically attractive or attractable plug of the light instrument allows simple positioning with respect to the light source and releasable connection to the magnetically attractable or attractive socket of the light source, since no interlocking mechanisms such as screw or bayonet connections need to be actuated for this purpose, and because of the magnetic attraction force between the plug of the light instrument and the socket of the light source only a small exertion of force by the operator is needed for its connection, or coupling, to the light source. The illumination system therefore has easy handling.

In a first variant, the socket of the light source preferably comprises a magnetisable material component or a magnetised material component, in which case the magnetisable material component may be magnetised in the socket of the light source. In a second variant, the socket of the light source comprises a magnetically attractable material component. In both variants, the material component of the socket of the light source is selected in such a way that the plug of the light instrument is magnetically attracted to the socket of the light source. This means that the material components of the plug of the light instrument, and respectively of the socket of the light source, are selected in such a way that a magnetic attraction force is provided between the two elements.

It is therefore conceivable for the plug of the light instrument to comprise a magnetically attractable material component, for example a particulate, in particular iron-containing, material component, and for the socket of the light source to comprise a magnetically attractive material component, preferably a magnetic material component. Such a design is preferred since the plug of the light instrument can in this case be produced economically and is therefore suitable, for example, as a disposable product for single use. It is, however, likewise conceivable for the plug of the light instrument to comprise a magnetically attractive material component, preferably a magnetic material component, and for the socket of the light source to comprise a magnetically attractable material component, for example a particulate, in particular iron-containing, material component.

In connection with the different materials or material components and their material properties, for example magnetisation or demagnetisation of the socket of the light source, reference is made to the explanations above in connection with the plug of the light instrument. These comments may be understood similarly for the materials or material components and properties of the socket of the light source.

Thus, the magnetisable material component and/or the magnetised material component of the illumination system, or of the socket of the light source, may consist of a ferrimagnetic and/or ferromagnetic material component.

In one particularly preferred embodiment, the magnetisable material component and/or the magnetised material component and/or the magnetically attractive material component is preferably particularly configured and is embedded in a plastic matrix. The plug of the light instrument is thus essentially produced from plastic with embedded magnetisable or magnetised particles. The plastic matrix is preferably produced by injection moulding or extrusion, in which case the particles can be embedded during the injection moulding or the extrusion.

As already mentioned, production of the plug of the light instrument as an injection-moulded or extruded part allows economical production in large batch numbers, and allows its use as a disposable part, which is of great importance particularly in respect of the requirements relating to hygiene and sterility of an operating theatre.

The socket of the light source may consist fully of the magnetisable material or of the magnetised material, or the magnetisable material component or the magnetised material component may be arranged only in regions, for example in the region of the distal end of the socket of the light source, particularly in the further abutment surface of the socket of the light source.

In particular, it is preferred for the plug of the light instrument to comprise a magnetisable material component or a magnetised material component in particle form, which is distributed at least in the region of its abutment surface or fully throughout the entire plug of the light instrument, and for the socket of the light source to comprise at least one magnet, or at least one solenoid, in the region of its further abutment surface.

The magnetised material component may be configured as at least one magnet or as at least one solenoid. In particular, the at least one magnet or the at least one solenoid may have a plastic material moulded around it in the manner of a sleeve.

The at least one magnet is in this case preferably a constant or permanent magnet.

The socket of the light source preferably comprises an essentially cylindrical body, which internally defines a cavity. The cavity may open into an entry orifice at the proximal end and into an exit orifice at the distal end of the socket of the light source, in which case the light guide may extend through the exit orifice, via the cavity, and at least partially through the cavity.

It is preferred that in this case the light guide is firmly mounted in the interior of the socket of the light source, particularly in the region of the entry and exit orifices of the socket of the light source.

It is preferred for the socket of the light source in the region of its cavity, as well as its cavity, respectively to have a constant diameter.

It is, however, also conceivable for the socket of the light source and/or its cavity to be configured to be conically convergent or conically divergent oppositely to one another or in the same way as one another.

An adjustment flange, the diameter of which is greater than the diameter of the essentially cylindrical body of the socket of the light source, may be arranged at the proximal end of the socket of the light source.

The adjustment flange is firmly fixed to the plug socket on the light instrument by means of a screw connection. By means of a fine screw thread between the socket body and the adjustment flange, the distance to the focusing lens can be adjusted in such a way that the proximal end of the light guide lies at the focal point. After adjustment, the adjustment flange may be fixed, and the plug socket, which with the adjustment flange is a component part of the plug socket, thus becomes an immovable component part of the light source.

The socket of the light source and the adjustment flange may in this case be configured as two separate parts.

The adjustment flange is preferably configured essentially with a T-shape in cross section and extends through the entry orifice of the socket of the light source at least partially into the cavity of the socket of the light source.

A through-orifice may extend centrally through the adjustment flange, through which orifice the light guide can be inserted into the cavity of the socket of the light source.

As described above, it is preferable for the light guide to be mounted in a guide tube, which extends through the plug and is firmly connected to the plug. Preferably, the guide tube extends with its proximal end out of the plug of the light instrument, so that the guide tube can be inserted into a socket. Particularly preferably, the proximal end of the guide tube protrudes from the plug over the same distance as the light guide itself. This means that the light guide, as seen from the abutment surface of the plug, is enclosed by the guide tube essentially over its entire length as seen from the abutment surface. The proximal end of the guide tube essentially comes to lie at the focal point.

The connected state in this case refers to the releasable connection of the light instrument, i.e. of the plug of the light instrument with the light guide, or additionally with the guide tube, to the socket of the light source. The releasable connection in this case occurs because of the magnetic attraction force between the plug of the light instrument and the socket of the light source. An unconnected state exists when the light instrument and the socket of the light source lie outside the range of their magnetic attraction force.

The magnetic attraction force may also be referred to as a magnetic pulling force, and may correspond to the force which is exerted by the magnetically attractive material component on the magnetically attractable material component.

A magnetic pulling force between the plug of the light instrument and the socket of the light source is preferably between 0.1 N and 5 N, preferably between 0.5 N and 2 N, or the magnetic pulling force is preferably equal to or greater than 2 N.

The plug of the light instrument and the socket of the light source may be configured to be magnetically attractable at a distance of between 1 mm and 30 mm, preferably between 5 mm and 20 mm, or the plug of the light instrument and the socket of the light source may be configured to be magnetically attractable over a distance of at least 10 mm, preferably at least 20 mm.

Preferably, the pulling force facilitates plugging of the plug over a certain distance. Consequently, the plug does not then need to be manually pushed to abutment, but instead the plug is automatically pulled to abutment as soon as the magnetic force acts.

It is preferred for the plug of the light instrument to be configured as a handle.

This facilitates and improves handling of the illumination system, since the operator can grip the plug of the light instrument in the configuration of a handle even when wearing operating gloves, and can subsequently connect it to the socket of the light source of the illumination device with only little exertion of force. At a short distance, the plug of the light instrument is automatically pulled onto the abutment of the socket of the light source.

BRIEF DESCRIPTION OF THE DRAWINGS

Preferred embodiments of the invention will be described below with the aid of the drawings, which are merely used for explanation and are not to be interpreted as restrictive. In the drawings:

FIG. 1b shows a perspective view of the plug connection of an ophthalmic illumination system with an ophthalmic light instrument and the socket of the light source in the unconnected state, with a light guide extending through a plug of the light instrument according to FIG. 1a;

DESCRIPTION OF THE INVENTION

Figure 1A:
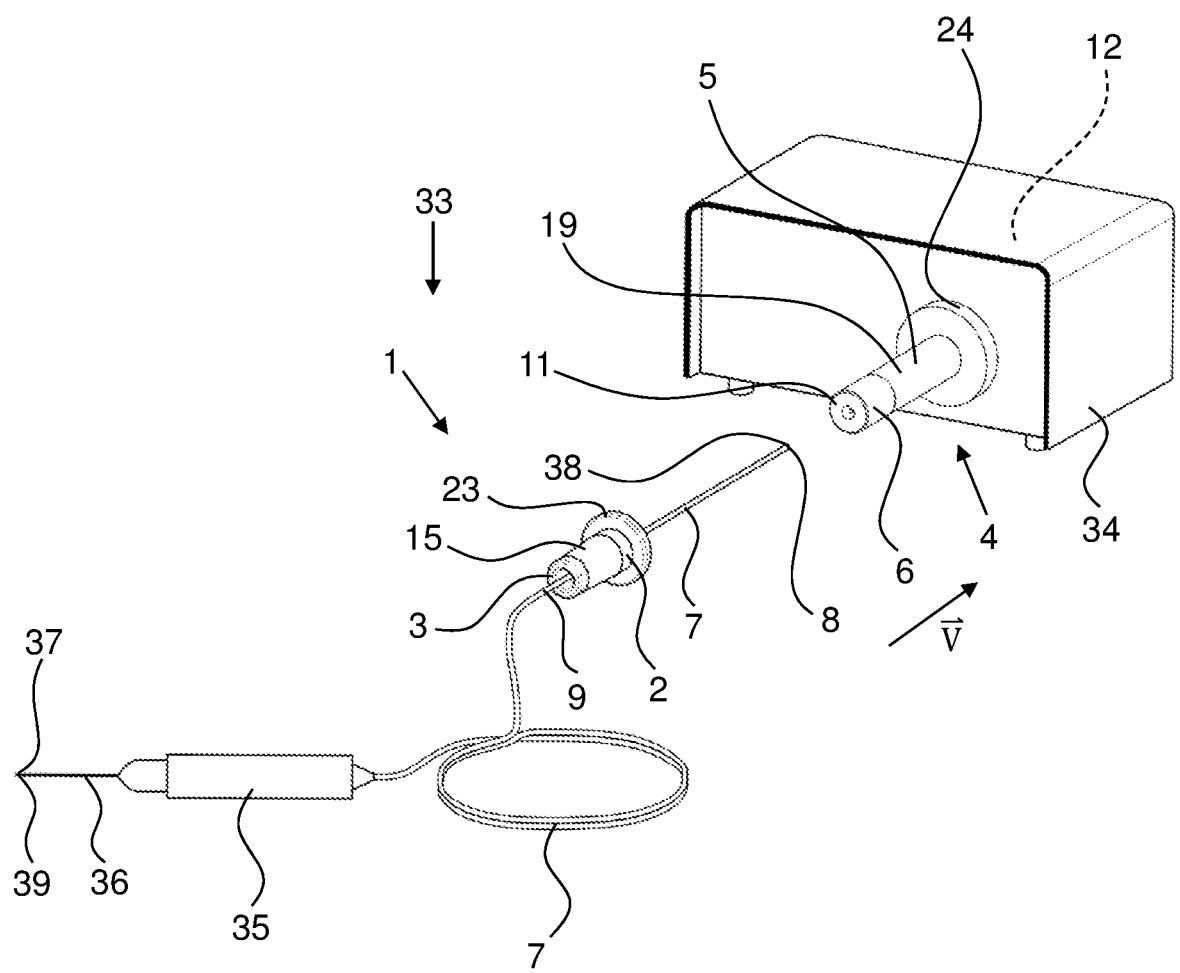
FIG. 1a shows a perspective view of an ophthalmic illumination system having a light instrument and a light source with a socket.

FIG. 1a shows an ophthalmic illumination system. The ophthalmic illumination system comprises a light instrument 33 with a plug 1, and a light source 12 with a socket 4. The light source 12 is in this case arranged in a housing 34 and the socket of the light source 4 is fastened firmly on the housing 34.

In the embodiment shown, the light instrument 33 is an illumination element which is provided exclusively for illumination. As an alternative, however, the light instrument may also be an integral part of an illuminated instrument, for example an illuminated cutter, an illuminated laser probe, illuminated forceps, etc.

The light instrument 33 is in this case represented as being separated from the socket of the light source 4 and from the housing 34. The light instrument 33 can, as will be described below, be connected to the socket of the light source 4 by means of the plug 1 of the light instrument.

In the embodiment shown, the light instrument 33 essentially comprises a handle 35, a light guide 7 and a plug 1 of the light instrument. The light guide 7, as described below, is firmly connected to the plug 1 of the light instrument, and light is coupled into the light guide by means of the light source 12. The light guide 7 is furthermore firmly connected to the handle 35 and the cannula 36. The handle 35 furthermore comprises a cannula 36, through which the light can then be output. Through the cannula 36, the light guide 7 in turn extends as far as the distal end 39 of the cannula 36. The distal end 37 of the light guide 7 lies at the distal end 39 of the cannula 36.

FIGS. 1b to 5 respectively show an ophthalmic illumination system with a plug of the light instrument and a socket of the light source, whereas only the plug of the light instrument is depicted in FIGS. 7 to 10.

The ophthalmic illumination system in this case comprises an ophthalmic light instrument as well as a light source with a socket 4. The light instrument in turn comprises a plug 1 of the light instrument with an abutment surface 23, as well as a light guide 7, mounted on the plug of the light instrument 1, for guiding light to a surgical site in the eye. The light guide 7 has a proximal end 8 for coupling of light 10 from a light source 12, as well as a distal end 37 for emission of the light 10 which has been put in. The distal end 37 of the light guide 7 in this case lies at the distal end 39 of the cannula 36. The cannula 36 can be moved to the site desired by the surgical staff during an operation procedure. The plug 1 of the light instrument is configured to be magnetically attractable or attractive, and the socket of the light source 4 is likewise configured to be magnetically attractable or attractive, and has a further abutment surface 11 so that the socket of the light source 4 can be positioned by means of its further abutment surface 11 with respect to the light source in such a way, and can be releasably connected to the abutment surface 23 of the plug 1 of the light instrument in such a way, that the proximal end 8 of the light guide 7 comes to lie at the focal point 14 of the light source 12, so that coupling of the light 10 into the light instrument takes place at the focal point 14 of the light source 12.

Figure 1B:
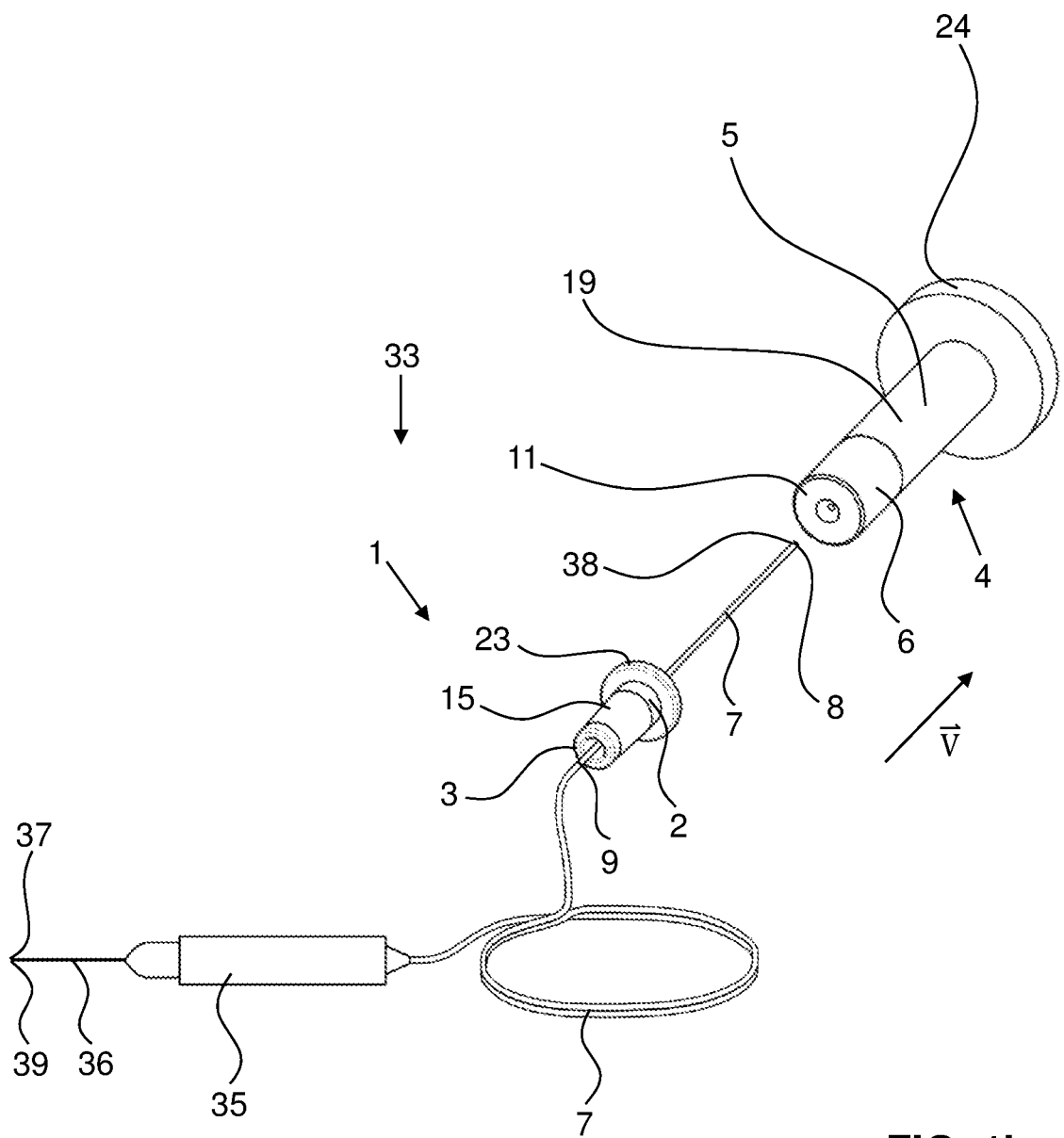
Figure 2:
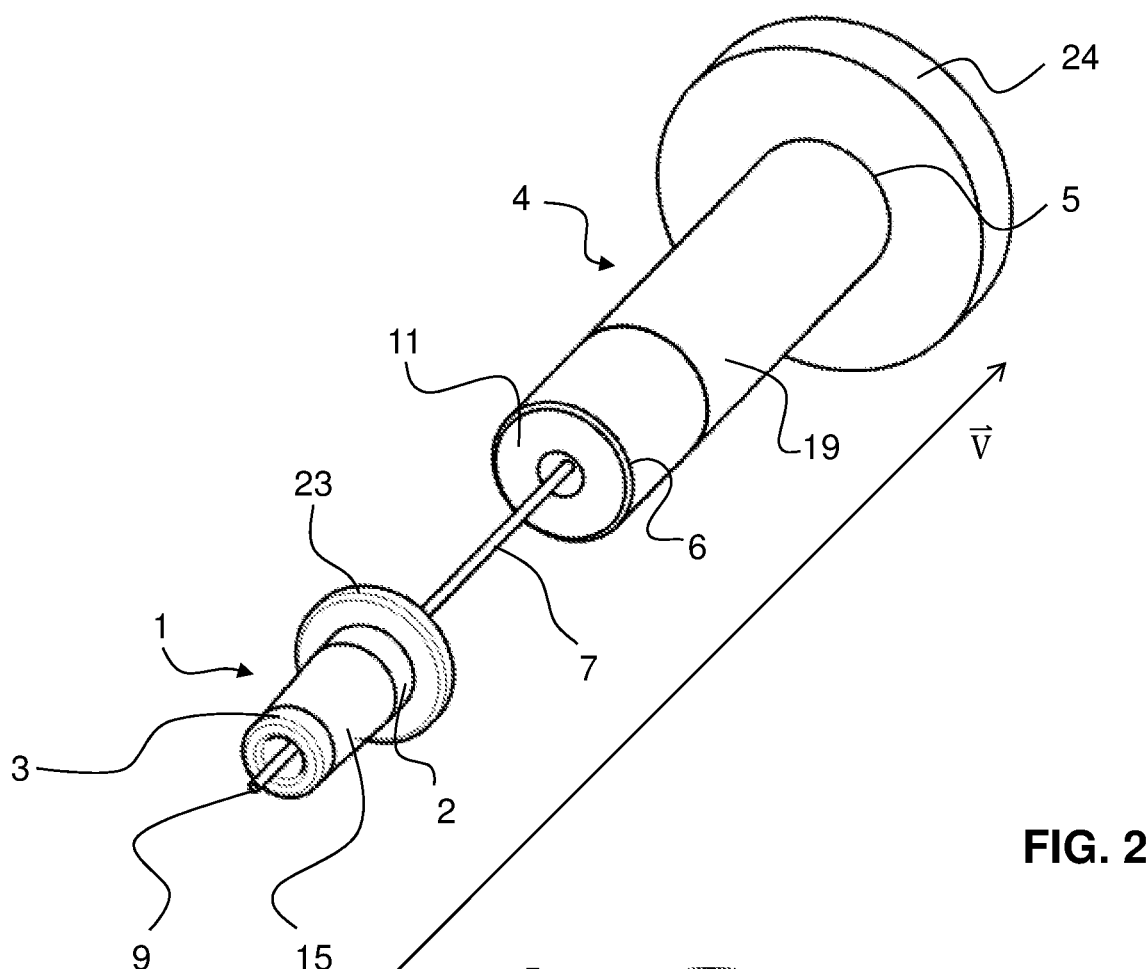
FIG. 2 shows a perspective view of the plug connection of the ophthalmic illumination system according to FIG. 1, with the light guide additionally extending into the socket of the light source.
Figure 3:
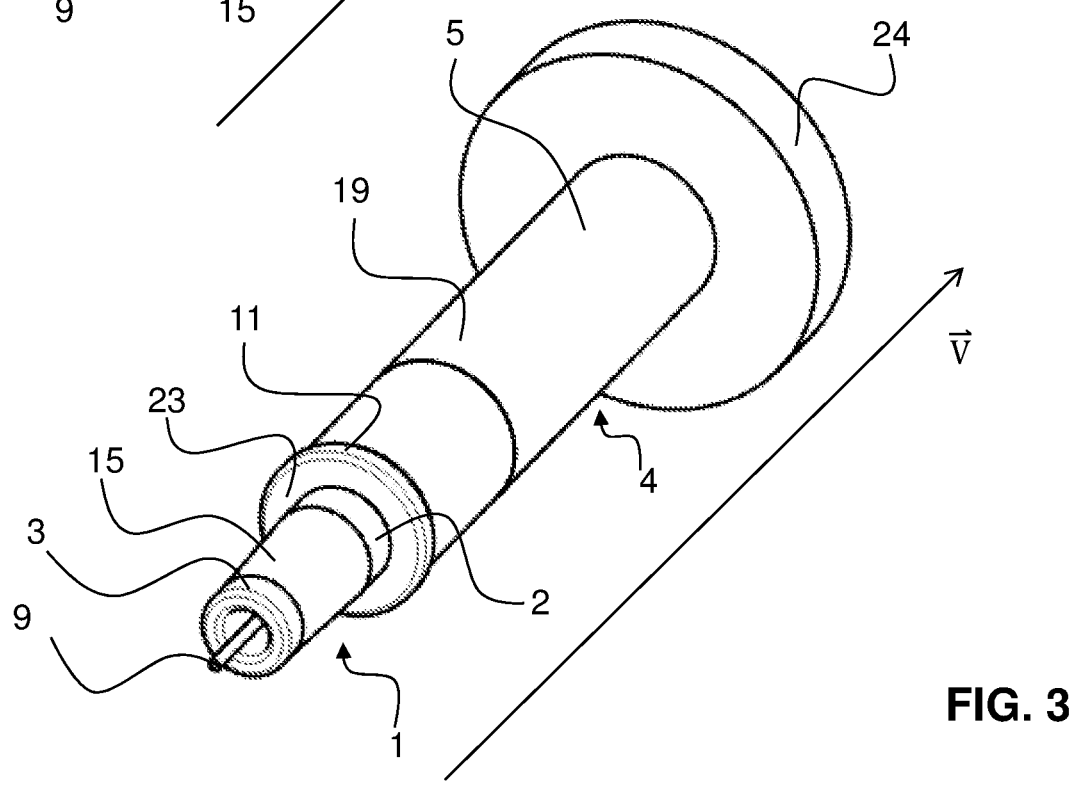
FIG. 3 shows a perspective view of the plug connection of an ophthalmic illumination system with the ophthalmic light instrument and the socket of the light source in the connected state.

This means that the socket of the light source 4 can be separate from the light instrument in an unconnected state according to FIGS. 1b and 2, and in a connected state according to FIG. 3.

In the unconnected state according to FIG. 1, the light guide 7 extends fully through the plug 1 of the light instrument and protrudes with its distal end 37 beyond the distal end 3 of the plug 1 of the light instrument and with its proximal end 8 beyond the proximal end 2 of the plug 1 of the light instrument. In order to connect the light instrument, i.e. in this case the plug 1 of the light instrument with the light guide 7, to the illumination system by the socket of the light source 4, the proximal end 8 of the light guide 7 is first inserted into the distal end 6 of the socket of the light source 4. This situation corresponds to the still unconnected illumination system according to FIG. 2. After the light guide 7 has been received not only in the plug 1 of the light instrument but at least partially also in the socket of the light source 4, and the socket of the light source 4 and the plug 1 of the light instrument lie within a certain distance d from one another, magnetic attraction between the magnetically attractable plug 1 of the light instrument and the magnetically attractive socket of the light source 4, or between the magnetically attractive plug 1 of the light instrument and the magnetically attractable socket of the light source 4, leads to connection of the plug 1 of the light instrument to the socket of the light source 4 along a connection direction V. This situation corresponds to the connected illumination system according to FIG. 3. In this connected state, the proximal end 2 of the plug 1 of the light instrument and the distal end 6 of the socket of the light source 4 bear in a planar manner on one another.

In order to separate the illumination system, i.e. to remove the plug 1 of the light instrument from the socket of the light source 4, the surgical staff member pulls the plug 1 of the light instrument counter to the connection direction V from the socket of the light source 4 until the abutment surface 23 of the plug 1 of the light instrument and the further abutment surface 11 of the socket of the light source 4 lie outside the range of the magnetic attraction force. The illumination system is then again in its unconnected state, and if required the plug of a new light instrument may be connected to the socket of the light source to form a new illumination system.

As revealed by the sectional views 4 and 5, the plug 1 of the light instrument has an essentially cylindrical body 15, which internally defines a cavity 16. The cavity 16 in this case opens into an entry orifice 17 at the proximal end 2 and into an exit orifice 18 at the distal end 3 of the plug 1 of the light instrument. The abutment surface 23 at the proximal end 2 of the plug 1 of the light instrument is configured as a flange, the diameter DF of which is greater than the diameter DS of the essentially cylindrical body 15 of the plug 1 of the light instrument. In these figures, the essentially cylindrical body 15 of the plug 1 of the light instrument and the abutment surface 23 configured as a flange are formed in one piece.

The cavity 16 in this case has two sections of different diameters. The first section opens into the entry orifice 17 at the proximal end 2 of the plug 1 of the light instrument, and has a diameter which corresponds essentially to the external diameter of the light guide 7. The second section follows on from this first section in the distal direction, and opens into the exit orifice 18 at the distal end 3 of the plug 1 of the light instrument, the second section having a diameter which is greater than the diameter in the first section.

This region of the plug of the light instrument, i.e. where the cavity 16 in the plug of the light instrument is formed, is configured to be conically convergent as seen along the distal direction, i.e. starting from the entry orifice 17 in the direction of the exit orifice 18 of the plug of the light instrument, whereas the cavity 16 formed therein is configured to be conically divergent along this distal direction in this region.

The socket of the light source 4 likewise has an essentially cylindrical body 19, which internally defines a cavity 20, the cavity 20 opening into an entry orifice 21 at the proximal end 5 and into an exit orifice 22 at the distal end 6 of the socket of the light source 4. Arranged at the proximal end 5 of the socket of the light source 4, there is an adjustment flange 24, the diameter DJ of which is greater than the diameter DB of the essentially cylindrical body 19 of the socket of the light source 4. As can be seen in these figures, the adjustment flange 24 is configured essentially with a T-shape in cross section and extends through the entry orifice 21 of the socket of the light source 4 at least partially into the cavity 20 of the socket of the light source 4. The adjustment flange furthermore has a through-orifice 25, which extends centrally through the adjustment flange 24, and the light guide 7 can be inserted through its orifice 25 into the cavity 20 of the socket of the light source 4. Whereas the plug 1 of the light instrument has a conically convergent plug body of the light instrument and its cavity is conically divergent, the socket of the light source 4 has a constant diameter in the region of its cavity 20.

The adjustment flange 24 is in this case connected to the socket 4 by means of a screw connection. By means of the screw connection, which is preferably a fine screw thread, the distance to the focusing lens of the light source 12 can be adjusted in such a way that the proximal end 8 of the light guide 7 lies in the focal plane. After adjustment, the adjustment flange 24 is fixed, and the socket 4 is then in a fixed and immovable position with respect to the light source.

Figure 4:
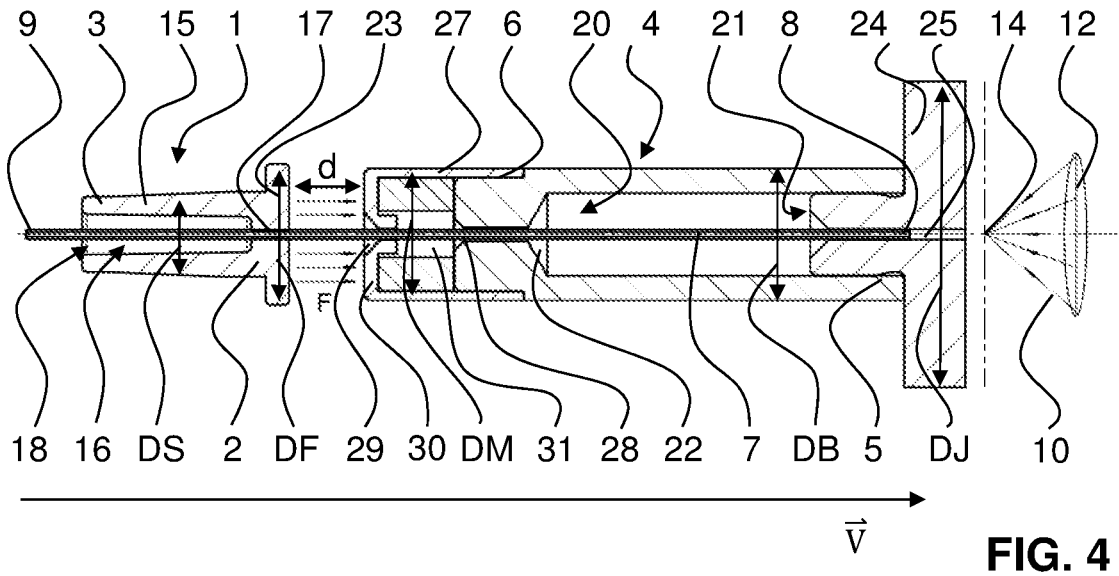
FIG. 4 shows a sectional view through the plug connection of the ophthalmic illumination system in the unconnected state according to FIG. 2.

In the still unconnected state according to FIG. 4, the light guide 7 extends with its distal end 37 through the entry orifice 17, via the cavity 16, through the exit orifice 18 of the plug 1 of the light instrument, fully through the plug 1 of the light instrument. With its proximal end 8, the light guide 7 extends through the exit orifice 22, via the cavity 20, and at least partially through the entry orifice 21 of the socket of the light source 4. In particular, the proximal region 8 of the light guide 7 is in this case at least partially inserted into the orifice 25 of the adjustment flange 24, but does not yet protrude beyond the proximal end of the adjustment flange 24, or the proximal end 5 of the socket 4.

As soon as the plug 1 of the light instrument and the socket of the light source 4 lie within a certain distance d from one another, the magnetic attraction force F between the magnetically attractive or attractable plug 1 of the light instrument, and respectively the socket of the light source 4, leads to full connection of the plug 1 of the light instrument to the socket of the light source 4, or respectively between their abutment surfaces 23, 11. The magnetic attraction between the plug 1 of the light instrument and the socket of the light source 4 in this case corresponds to a magnetic pulling force of between about 0.5 N and 2 N, so that the plug 1 of the light instrument and the socket of the light source 4 can be magnetically attracted at a distance d of between about 5 mm and 20 mm.

Although different configurations of the magnetically attractably or magnetically attractively configured plug 1 of the light instrument and of the magnetically attractably or magnetically attractively configured socket of the light source 4 are possible in the scope of the present invention, the plug, as shown in the figures, of the light instrument 1 comprises particulate magnetisable material or magnetised material which has been produced by injection moulding or extrusion into a plastic matrix. If a strong magnetic field is applied during the injection moulding or extrusion, then the magnetisable material becomes magnetised, whereas if no magnetic field is applied, the magnetisable material does not become magnetised. The plug 1 of the light instrument is in this case produced entirely from plastic in which magnetisable or magnetised particles are incorporated. The socket of the light source 4 in this case comprises in the region of its distal end 6 the magnetised material in the form of a permanent magnet 26, which is enclosed by a sleeve of metal or plastic. The permanent magnet 26 is in this case configured in the shape of a ring and fully encircles the light guide 7. The diameter DM of the permanent magnet and the diameter DB of the socket of the light source 4 in the region of its distal end 6, where the permanent magnet 26 comes to lie, are somewhat smaller than the diameter DB of the socket of the light source 4 in the region of its cavity 20, so that the socket 27 comes to lie in the manner of a cover over the permanent magnet 26, while following on without interruption from the distal end 6 of the sleeve of the light source 4. In other words, the sleeve 27 therefore has the same diameter as the socket of the light source 4 in the region of its cavity 20, and the sleeve 27 therefore forms with its end side the further abutment surface 30 for the abutment surface 23 of the plug 1 of the light instrument. The sleeve 27 likewise has a cavity 31, which opens in the proximal direction into an entry orifice 28 and in the distal direction into an exit orifice 29.

Thus, if the illumination system has a socket of the light source 4 with a sleeve 27 moulded on, then the light guide 7 contained in the connected state extends along the connection direction V, which corresponds to the proximal direction, from the exit orifice 18 of the plug 1 of the light instrument, via its cavity 16, through its entry orifice 17, into the exit orifice 29 of the sleeve 27, further via its cavity 31 through its entry orifice 28 into the exit orifice 22 of the socket of the light source 4, and further via its cavity 20 through the orifice 25 in the adjustment flange 24 and through the entry orifice 21 of the socket of the light source 4, and proximally out of the socket of the light source 4.

Figure 5:
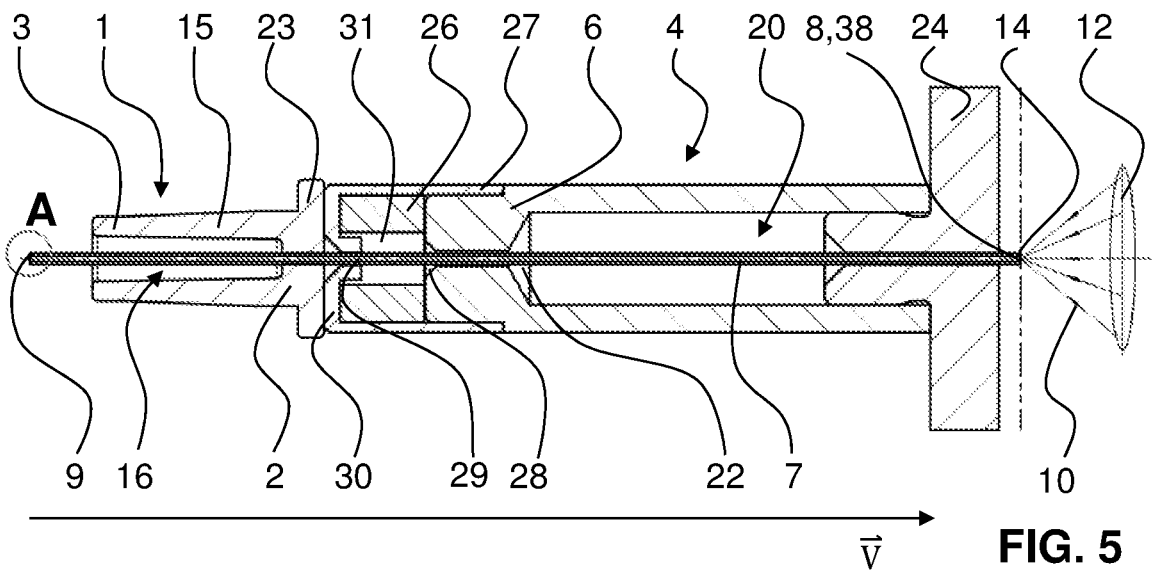
FIG. 5 shows a sectional view through the plug connection of the ophthalmic illumination system in the connected state according to FIG. 3.

As revealed by FIG. 5, the abutment surface 23 of the plug 1 of the light instrument and the further abutment surface 30 of the sleeve 27 then bear in a planar manner on one another, and the proximal end 8 of the light guide 7 lies at the focal point 14 of the light source 12, so that coupling of the light 10 into the light instrument takes place at the focal point 14 of the light source 12. This is light 10 from a light source 12 which focuses the emitted light 10 onto the focal point 14 by means of a lens.

Preferably, the light guide 7 is firmly connected to the plug by means of a guide tube 13. In the embodiment shown, the guide tube 13 extends from the proximal end 8 of the light guide 7 through the plug 1 of the light instrument. The guide tube 13 in this case comprises a distal end 9, out of which the light guide then protrudes as shown in FIGS. 1a and 1b. The proximal end 8 of the light guide 7 in this case lies in the region of the proximal end 38 of the guide tube 13.

Figure 6:
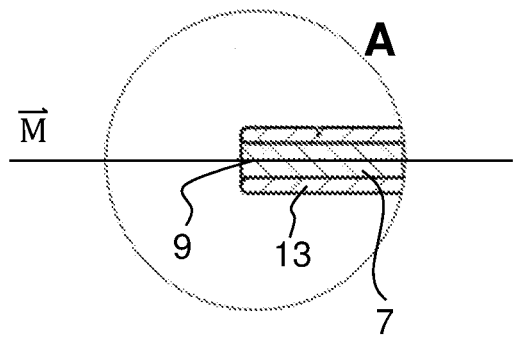
FIG. 6 shows a detailed view of the region A according to FIG. 5.
Figure 7:
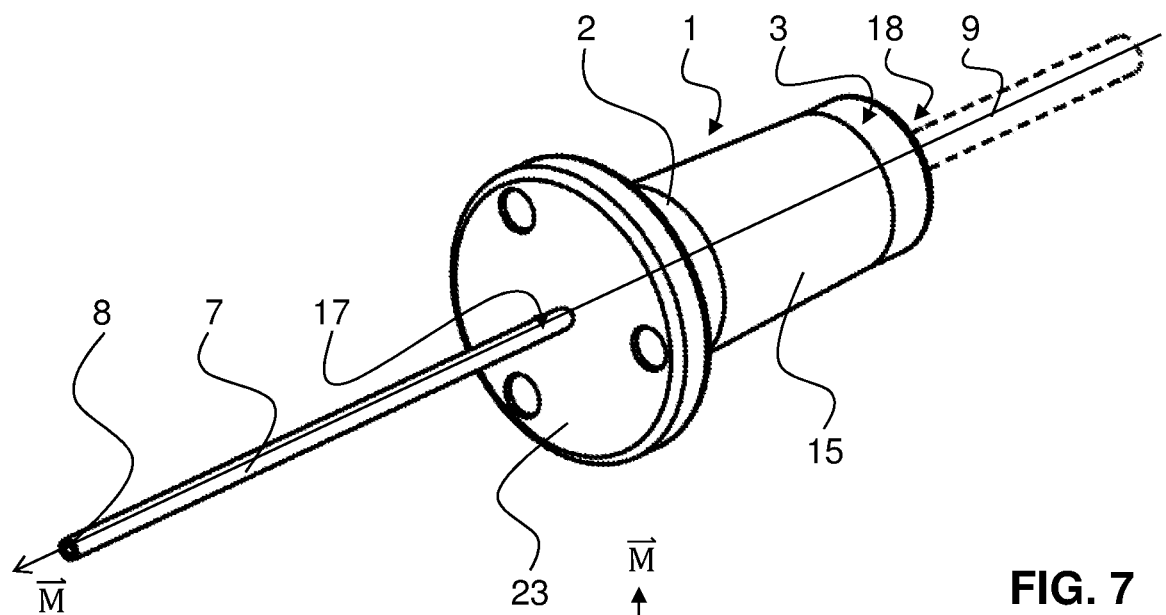
FIG. 7 shows a perspective view of the plug of the light instrument, with the light guide extending through the plug of the light instrument.
Figure 8:
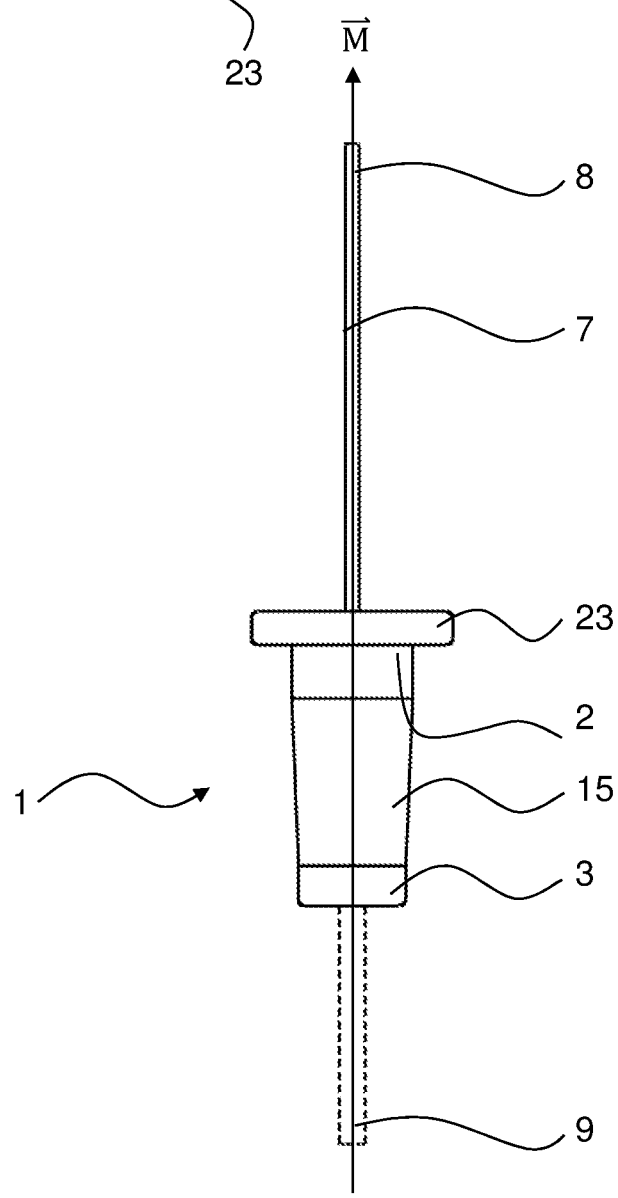
FIG. 8 shows a sectional view through the plug of the light instrument with the light guide according to FIG. 7.
Figure 9:
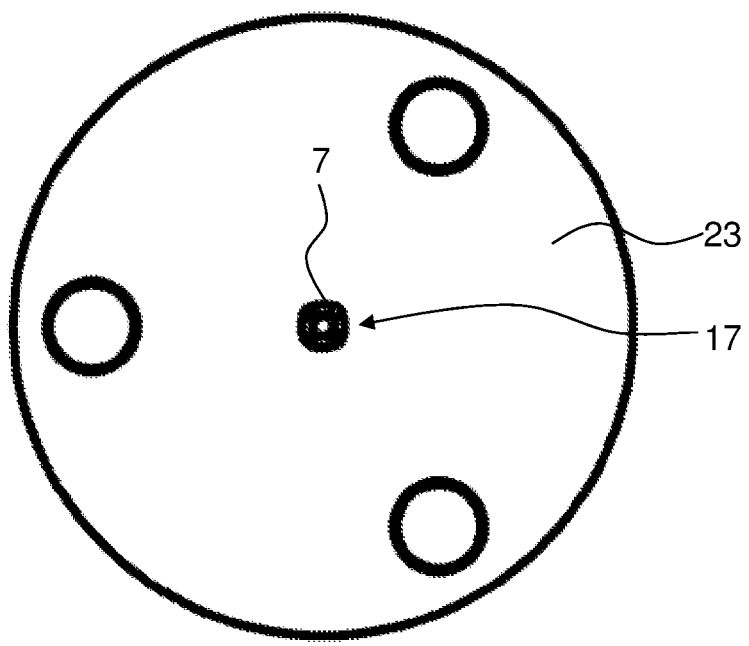
FIG. 9 shows a sectional view through the proximal end of the plug of the light instrument.
Figure 10:
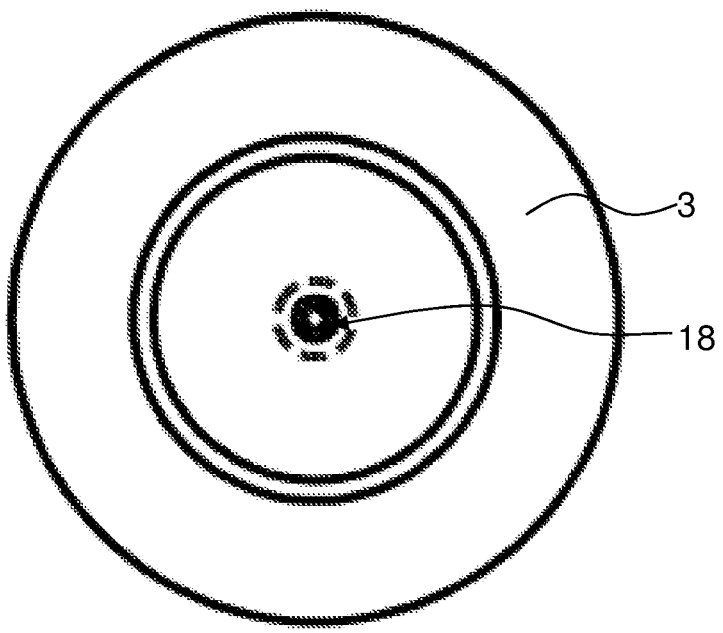
FIG. 10 shows a sectional view through the distal end of the plug of the light instrument.

FIG. 6 shows a detailed view of the region A according to FIG. 5, from which it can be seen that the guide tube 13 for receiving and guiding the light guide 7 can be functionally connected to the plug 1 of the light instrument and to the socket of the light source 4. This guide tube 13 encloses the light guide 7 in the manner of a sleeve, and therefore extends like the light guide 7 through the exit orifice 18 of the plug 1 of the light instrument, into its cavity 16, through its entry orifice 17, further through the exit orifice 22 of the socket of the light source 4, through its cavity 20, and, when the illumination system is in the connected state, through its entry orifice 21 and proximally out of the socket of the light source 4.

As revealed in particular by FIGS. 7 to 10, the guide tube 13 may be regarded as a guide for the light guide 7, this guide essentially being configured rotationally symmetrically around a mid-axis M and extending centrally through the plug 1 of the light instrument and the socket of the light source 4. From the distal end of the guide tube 13, the light guide 7 contained therein protrudes and is guided through the handle 35 to the distal end 39 of the cannula 36. This cannula 36 may, with the light guide 7 lying inside it, be inserted into the eye for illumination purposes.

The invention claimed is:

1. An ophthalmic light instrument, comprising
a plug of the light instrument, having an abutment surface that is formed at a proximal end of the plug of the light instrument; and
a light guide, mounted on the plug of the light instrument, for guiding light to a surgical site in the eye, wherein the light guide has a proximal end for coupling of light from a light source and a distal end for emission of light,
wherein at least the abutment surface of the plug of the light instrument is configured to be magnetically attractable or attractive such that the plug can be positioned by its abutment surface with respect to the light source in such a way, and can be connected releasably by its abutment surface to the light source in such a way, that the proximal end of the light guide comes to lie at a focal point of the light source, so that coupling of the light into the light instrument takes place at the focal point of the light source,
wherein at least the abutment surface of the plug of the light instrument comprises a magnetisable material component or a magnetised material component, or wherein at least the abutment surface of the plug of the light instrument comprises a magnetically attractable material component,
wherein at least one of the magnetisable material component and the magnetised material component and the magnetically attractive material component is a particulate and is embedded in a plastic matrix such that a magnetic attraction takes place between the abutment surface of the plug of the light instrument and the light source, which positions or holds the plug of the light instrument with respect to the light source in such a way that the coupling of light into the light instrument takes place at the focal point of the light source, and
wherein the magnetic attraction being established between the abutment surface and the light source pulls the light instrument into the focal point of the light source.

2. The light instrument according to claim 1, wherein at least one of the magnetisable material component in the plug of the light instrument is magnetised, and
the magnetisable material component and the magnetised material component comprises a ferrimagnetic material component, and
the magnetisable material component and the magnetised material component comprises a ferromagnetic material component.

3. The light instrument according to claim 1, wherein particles can be embedded during injection molding or extrusion.

4. The light instrument according to claim 1, wherein the plug of the light instrument fully comprises the magnetisable material component or the magnetised material component, or
wherein at least one of the magnetisable material component or the magnetised material component is arranged in the region of the proximal end of the plug of the light instrument, and the plug of the light instrument additionally comprises a magnetised material component being configured as at least one magnet or as at least one solenoid.

5. The light instrument according to claim 1, wherein the plug of the light instrument comprises an essentially cylindrical body, which internally defines a cavity,
wherein the cavity opens into an entry orifice at the proximal end and into an exit orifice at the distal end of the plug of the light instrument, and wherein the light guide extends through the entry orifice, via the cavity, and through the exit orifice.

6. The light instrument according to claim 5, wherein an abutment surface at the proximal end of the plug of the light instrument is configured as a flange, the diameter of which is greater than or equal to the diameter of the essentially cylindrical body of the plug of the light instrument.

7. The light instrument according to claim 1, wherein the light guide is firmly mounted on or in the plug.

8. An ophthalmic illumination system comprising a light instrument according to claim 1 and a socket of the light source, having a further abutment surface,
wherein the socket of the light source is configured to be magnetically attractable or attractive, and wherein the abutment surface of the plug comes in contact with the further abutment surface of the socket, wherein the abutment surface of the plug rests on the further abutment surface of the socket, wherein a magnetic attraction is established between the abutment surface of the plug and the socket so that the light guide is positioned with respect to the light source in such a way, and can be connected releasably to the plug of the light instrument in such a way, that the proximal end of the light guide comes to lie at the focal point of the light source, so that coupling of light takes place at the focal point of the light source, and wherein the magnetic attraction being established between the abutment surface of the plug and the socket pulls the light instrument into the focal point of the light source.

9. The illumination system according to claim 8, wherein the socket of the light source comprises a magnetisable material component or a magnetised material component or a magnetically attractable material component, and wherein the material component of the socket of the light source is selected in such a way that the plug of the light instrument is magnetically attracted towards the socket of the light source.

10. The illumination system according to claim 9, wherein at least one of the magnetisable material component in the socket of the light source is magnetised, and
the magnetisable material component and the magnetised material component and the magnetically attractable material component is particulate and is embedded in a plastic matrix, wherein particles can be embedded during injection molding or extrusion, and
the magnetisable material component or the magnetised material component is arranged in a region of the distal end of the socket of the light source, and
the magnetised material component is configured as at least one magnet or as at least one solenoid.

11. The illumination system according to claim 8, wherein the socket of the light source comprises an essentially cylindrical body, which internally defines a cavity,
wherein the cavity opens into an entry orifice at a proximal end and into an exit orifice at a distal end of the socket of the light source, and
wherein the light guide extends through the exit orifice, via the cavity, and at least partially through the entry orifice.

12. The illumination system according to claim 11, wherein an adjustment flange, a diameter of which is greater than a diameter of the essentially cylindrical body of the socket of the light source, is arranged at the proximal end of the socket of the light source.

13. The illumination system according to claim 12, wherein the adjustment flange is configured essentially with a T-shape in cross section and extends through the entry orifice of the socket of the light source at least partially into the cavity of the socket of the light source, and
wherein a through-orifice extends centrally through the adjustment flange, through which orifice the light guide can be inserted into the cavity of the socket of the light source.

14. The illumination system according to claim 8, wherein a magnetic pulling force between the plug of the light instrument and the socket of the light source lies between 0.1 N and 5 N, or
wherein at least one of the magnetic pulling force is equal to or greater than 2 N, and the plug of the light instrument and the socket of the light source are configured to be magnetically attractable at a distance of between 1 mm and 30 mm, or
wherein the plug of the light instrument and the socket of the light source are configured to be magnetically attractable over a distance of at least 10 mm.

15. A light instrument according to claim 1, wherein the plastic matrix is produced by injection moulding or extrusion, and wherein the magnetisable material component is magnetised during the injection moulding or during the extrusion or after the injection moulding, respectively by application of a magnetic field.

16. The light instrument according to claim 4, wherein at least one of the magnetisable material component or the magnetised material component is arranged in an abutment surface of the plug of the light instrument.

17. The light instrument according to claim 7, wherein the light guide is firmly mounted in the plug by means of a guide tube which extends through the plug.

18. The illumination system according to claim 10, wherein the plastic matrix is produced by injection moulding or extrusion, wherein the magnetisable material component is magnetised during the injection moulding or during the extrusion or after the injection moulding, respectively by application of a magnetic field, and wherein the magnetisable material component or the magnetised material component is arranged in the further abutment surface of the socket of the light source.

19. The illumination system according to claim 14, wherein the magnetic pulling force between the plug of the light instrument and the socket of the light source lies between 0.5 N and 2 N, or
wherein the plug of the light instrument and the socket of the light source are configured to be magnetically attractable at a distance of between 5 mm and 20 mm, or
wherein the plug of the light instrument and the socket of the light source are configured to be magnetically attractable over a distance of at least 20 mm.

20. An ophthalmic light instrument comprising:
a plug of the light instrument, having an abutment surface that is formed at a proximal end of the plug of the light instrument; and
a light guide, mounted on the plug of the light instrument, for guiding light to a surgical site in the eye, wherein the light guide has a proximal end for coupling of light from a light source and a distal end for emission of light,
wherein at least the abutment surface of the plug of the light instrument is configured to be magnetically attractable or attractive such that the plug is configured to be positioned by its abutment surface with respect to the light source in such a way, and can be connected releasably by its abutment surface to the light source in such a way, that the proximal end of the light guide comes to lie at the focal point of the light source, so that coupling of the light into the light instrument takes place at the focal point of the light source, wherein:

the plug of the light instrument defines a cavity having at least a first section opening into an entry orifice at the proximal end of the plug and a second section opening into an exit orifice at the distal end of the plug, wherein the light guide extends through the cavity, wherein the second section, which follows the first section when seen along a distal direction extending from the proximal end of the plug towards a distal end of the plug, has a diameter which is greater than a diameter of the first section, and wherein the cavity is conically divergent starting from the entry orifice towards the exit orifice when seen along the distal direction.

21. The illumination system according to claim 12, wherein the adjustment flange is connected to the socket via a screw connection, and wherein the screw connection enables an adjustment of a distance to the light source in such a way that the proximal end of the light guide lies in a focal plane of the light source.

\* \* \* \* \*